(12) United States Patent
Tsubamoto et al.

(10) Patent No.: US 7,081,473 B2
(45) Date of Patent: Jul. 25, 2006

(54) AGENT FOR PREVENTING/AMELIORATING OBESITY COMPRISING METHYLIDENE HYDRIZIDE COMPOUND AS ACTIVE INGREDIENT

(75) Inventors: Yoshiharu Tsubamoto, Nagoya (JP); Akira Tashita, Shiojiri (JP); Yukari Kobara, Masuda (JP); Takuji Kakigami, Inabe (JP)

(73) Assignee: Sanwa Kagaku Kenkyusho Co., Ltd., Nagoya (JP)

( * ) Notice: Subject to any disclaimer, the term of this patent is extended or adjusted under 35 U.S.C. 154(b) by 0 days.

(21) Appl. No.: 10/514,027

(22) PCT Filed: May 20, 2003

(86) PCT No.: PCT/JP03/06247

§ 371 (c)(1),
(2), (4) Date: Jan. 5, 2005

(87) PCT Pub. No.: WO03/097031

PCT Pub. Date: Nov. 27, 2003

(65) Prior Publication Data

US 2005/0159415 A1    Jul. 21, 2005

(30) Foreign Application Priority Data

May 22, 2002    (JP)    ............... 2002-147751

(51) Int. Cl.
| A61K 31/166 | (2006.01) |
| A61K 31/4045 | (2006.01) |
| A61P 3/04 | (2006.01) |
| C07C 243/18 | (2006.01) |
| C07D 209/08 | (2006.01) |
| C07D 409/06 | (2006.01) |

(52) U.S. Cl. ................ 514/415; 514/419; 514/615
(58) Field of Classification Search ................ 548/465, 548/495; 564/174; 514/415, 419, 615
See application file for complete search history.

(56) References Cited

FOREIGN PATENT DOCUMENTS

| WO | WO 99/01423 A1 | 1/1999 |
| WO | WO 00/39088 A1 | 7/2000 |
| WO | WO 01/87341 A1 | 11/2001 |
| WO | WO 02/00612 A1 | 1/2002 |

OTHER PUBLICATIONS

Kazumasa Miyawaki et al., "*Inhibition of GIP Signaling Prevents Obesity*," Abstracts from the ADA 61st Scientific Sessions (2001), Abstract No. 335-PP, pp. A83-A84.

Margaret A. Cascieri, et al. "*Characterization of a Novel, Non-Peptidyl Antagonist of the Human Glucagon Receptor*," The Journal of Biological Chemistry, 1999 The American Society of Biochemistry and Molecular Biology, Inc., vol. 274, No. 13, Issue of Mar. 25, pp. 8694-8697.

Anthony Ling, et al., "*Identification of Alkylidene Hydrazides as Glucagon Receptor Antagonists*," Journal of Medical Chemistry, 2001, vol. 44, No. 19, pp. 3141-3149.

Primary Examiner—Fiona T. Powers
(74) Attorney, Agent, or Firm—Burr & Brown

(57) ABSTRACT

The present invention provides a low-molecular inhibitor of GIP functions and, further, an agent for preventing/ameliorating obesity based on inhibition of GIP functions, which comprises, as an active ingredient, a compound represented by the following general formula (I):

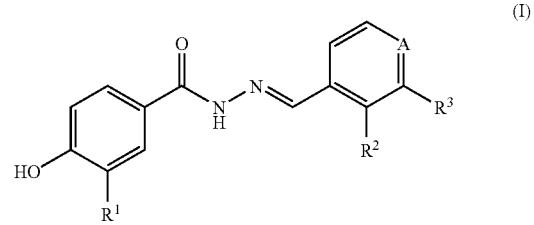

(I)

(wherein $R^1$ represents hydrogen, halogen, a nitro group or a cyano group, $R^2$ and $R^3$ each represent hydrogen or halogen, hydrogen or a methoxy group, or both $R^2$ and $R^3$ may form an optionally substituted benzene or pyrrole ring, and A represents nitrogen or C—$R^4$ whereupon $R^4$ represents hydrogen, an optionally substituted C1 to C6 alkyl group, —$OR^7$, —$NR^8R^9$, —NHCO—$R^{10}$ or —$SO_2$—$R^{11}$ or may, together with $R^3$, form an optionally substituted benzene or pyrrole ring, $R^7$, $R^8$ and $R^9$ each represent hydrogen or an optionally substituted C1 to C6 alkyl group, $R^{10}$ represents a C1 to C6 alkyl group or the like, and $R^1$ represents an optionally substituted morpholyl group or the like) or a pharmaceutically acceptable salt thereof.

8 Claims, 1 Drawing Sheet

US 7,081,473 B2

AGENT FOR PREVENTING/AMELIORATING OBESITY COMPRISING METHYLIDENE HYDRIZIDE COMPOUND AS ACTIVE INGREDIENT

TECHNICAL FIELD

The present invention relates to a GIP function inhibitor comprising a previously known methylidene hydrazide compound as an active ingredient and, further, to an agent for preventing/ameliorating obesity.

BACKGROUND ART

Glucose dependent-insulinotropic polypeptide, also known as, gastric inhibitory polypeptide (hereinafter, abbreviated to GIP) is one of the gastrointestinal hormones belonging to a glucagon/secretin family. GIP, together with glucagon-like peptide 1 (GLP-1), is referred to as incretin and secreted from K cells present in the small intestine upon ingestion, and promotes the secretion of insulin by glucose in pancreatic β cells, thereby controlling the movement of nutrients in the living body upon ingestion. In addition, GIP is estimated to inhibit stomach motility and to stimulate intestinal secretion. However, its initially found inhibitory action on secretion of gastric acid is questionable at present. A GIP receptor gene is expressed widely not only in pancreatic β cells and adipocytes but also in other cells, and it is thus estimated that GIP also act in other tissues, which is however not fully elucidated.

Obesity is a lifestyle-related disease increasing due to westernization of the dietary habits of the Japanese at present, and is a risk factor of lifestyle-related diseases such as fatty liver, diabetes, gout, hypertension and arteriosclerosis. Medically, obesity is recognized as a morbid state of abnormal accumulation of fat resulting from relatively excessive ingestion of calories caused by hereditary and environmental factors, and is regarded as a subject of medical treatment. Treatment of obesity is carried out by combination of dietary cure and exercise cure, and an appetite inhibitor is rarely used. In Japan, a clinically used remedy for preventing or ameliorating obesity is only madindol (sanolex), while studies on other remedies such as β3 adrenaline receptor agonists, central nervous agonists, inhibitors of digestion and absorption, inhibitors of lipid synthesis, and leptin are advancing.

Madindol, which is commercially available as an adjunctive agent in dietary/exercise cures for severe obesity, is an appetite suppressant that act on the central nervous system, but its clinical effect is insufficient, and owing to the action on the central nervous system, the problem of dependence is pointed out. Other appetite suppressants working in the central nervous system, which act by different mechanisms, have been developed, but side effects in the central nervous system, such as increase in blood pressure, anxiety and headache, are worried about. A lipase inhibitor (orlistat), working mainly for inhibiting absorption of lipid and the like, is not reported to have severe side effects, but side effects such as fatty stools and flatus are reported. Leptin was expected as a promising candidate for a therapeutic agent for obesity because of its inhibitory effect on increase in body weight by decreasing food intake and accelerating energy consumption, but clinical tests revealed that the therapeutic effect is limited. β3-Receptor agonists are also expected as anti-obesity medicines, but their high receptor selectivity is essential, and side effects on the heart and the like are worried about if the selectivity is insufficient.

As described above, anti-obesity medicines based on various working mechanisms are commercially available or under development, but there are no medicines having both sufficient inhibitory effect on body weight gain and safety.

There are few studies on the relationship between GIP and obesity, but in recent years, the relationship is being elucidated. That is, a high-fat diet loading test on GIP receptor gene-deficient mice, conducted in a process for investigating the functions of GIP, revealed that obesity, occurring in wild-type mice, was inhibited in the GIP receptor gene-deficient mice (K. Miyawaki et al., "Inhibition of GIP Signaling Prevents Obesity", abstract #335-PP, the 61st Scientific Sessions of American Diabetes Association (2001)). When these GIP receptor gene-deficient mice were given conventional diet, the mice showed no difference from the wild-type mice in body weight change, thus suggesting that inhibiting the functions of GIP causes no adverse influence. It is also revealed that even in ob/ob mice, which are animals with hereditary obesity, obesity can be inhibited by making the mice deficient in the GIP receptor gene (see WO 01/87341).

From the foregoing, GIP was suggested to cause obesity with a new mechanism not proposed up to now, and compounds inhibiting the functions of GIP, for example antagonists of GIP receptors and inhibitors of GIP production, are promising as safe medicines having an anti-obesity effect.

Examples of the compounds inhibiting the functions of GIP may include GIP receptor antagonists such as GIP (6–30) —$NH_2$ (Regulatory Peptide, Vol. 69, pp. 151–154, 1997) and GIP(7–30) —$NH_2$ (Am. J. Physiol., 1999, Vol. 276, pp. E1049–54). However, these compounds are long-chain peptides and problematic in oral absorptivity and stability in blood, and are not suitable as anti-obesity agents. Besides these peptides, 3-bromo-5-methyl-2-phenylpyrazolo[1,5-a]pyrimidin-7-ol disclosed in WO 01/87341 is mentioned as a low-molecular compound inhibiting the functions of GIP, but its inhibitory activity is weak because its $IC_{50}$ is about 40 μM. As described above, a low-molecular compound strongly inhibiting the functions of GIP is still not known.

GIP, together with glucagon and GLP-1, is known as gastrointestinal hormone belonging to the glucagon/secretin family, and their primary amino acid sequences are highly homologous. The primary sequences of their receptor proteins are also highly homologous. However, whether or not a low-molecular inhibitor of functions of glucagon, for example, acts as an inhibitor of functions of GIP and/or GLP-1 is not evident. For example, L-168,049 known as a very potent antagonist of glucagon is considerably poor in an ability to bind to receptor for GLP-1, having the highest homology to glucagon (Margaret A. Cascieri et al., J. Biol. Chem., Vol. 274(13), 8694–8697 (1999)). The ability of L-168,049 to bind to GIP receptor is not described therein. Compounds disclosed in WO 02/00612 have a strong antagonistic activity on receptors of only glucagon, as compared with GIP and GLP-1. Further, compounds exhibiting a glucagon antagonistic activity, disclosed in WO 00/39088, are not known to have an antagonistic activity on GIP receptor. It is thus not possible to predict whether the antagonists for glucagon, belonging to the same family, act as GIP antagonists.

It is an object of the present invention to provide a low-molecular inhibitor of GIP functions and, further, an agent for preventing/ameliorating obesity in a new mechanism based on inhibition of GIP functions.

DISCLOSURE OF THE INVENTION

The present inventors made extensive studies for developing a medicine inhibiting a phenomenon caused by the action of GIP on cells expressing its receptor and, as a result, they found that methylidene hydrazide compounds known as a potent antagonist of glucagon has a new activity of inhibiting the functions of GIP. As a result of further studies on the basis of this finding, the present invention was completed.

That is, the present invention is directed to a GIP function inhibitor or an agent for preventing/ameliorating obesity, which comprises, as an active ingredient, a compound represented by the following general formula (I):

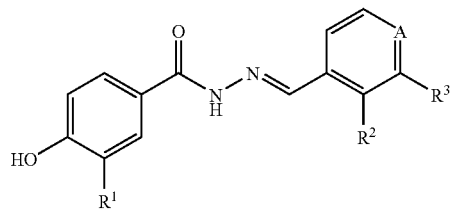

(I)

(wherein $R^1$ represents hydrogen, a halogen atom, a nitro group or a cyano group, $R^2$ represents hydrogen or a halogen atom or may, together with $R^3$, form an optionally substituted benzene ring or an optionally substituted pyrrole ring, $R^3$ represents hydrogen or a methoxy group or may, together with $R^2$, form an optionally substituted benzene ring or an optionally substituted pyrrole ring or may, together with $R^4$, form an optionally substituted benzene ring or an optionally substituted pyrrole ring, and A represents a nitrogen atom or C—$R^4$ whereupon $R^4$ represents hydrogen, an optionally substituted C1 to C6 alkyl group, —$OR^7$, —$NR^8R^9$, —NHCO—$R^{10}$ or —$SO_2$—$R^{11}$ or may, together with $R^3$, form an optionally substituted benzene ring or an optionally substituted pyrrole ring, $R^7$, $R^8$ and $R^9$ independently represent hydrogen or an optionally substituted C1 to C6 alkyl group, $R^{10}$ represents a C1 to C6 alkyl group, a C3 to C6 cycloalkyl group, an optionally substituted furyl group, an optionally substituted thienyl group, an optionally substituted benzyl group, an optionally substituted benzyloxymethyl group, an optionally substituted phenylvinyl group or an optionally substituted phenoxymethyl group, and $R^{11}$ represents an optionally substituted morpholyl group, an optionally substituted cyclopentylamino group, an optionally substituted piperidinyl group or a diethylamino group) or a pharmaceutically acceptable salt thereof.

The present invention provides a low-molecular compound inhibiting the functions of GIP. The present invention also provides an agent for preventing/ameliorating obesity based on a new mechanism of inhibiting the functions of GIP, which has never been achieved.

BEST MODE FOR CARRYING OUT THE INVENTION

Figure 1:
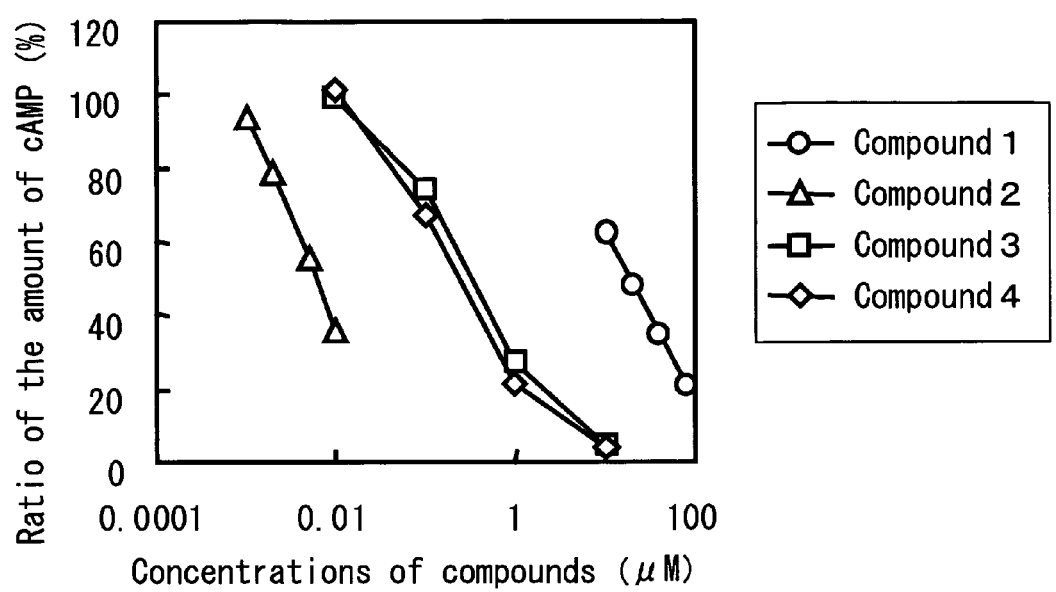
FIG. 1 is a graph showing the ratio of the amount of cAMP formed upon addition of each compound in Pharmacological Test Example 1 in this specification to the amount of cAMP formed in the absence of the compound.

Hereinafter, description will be given of a methylidene hydrazide compound used in the present invention in detail. The methylidene hydrazide compound inhibiting the functions of GIP used in the present invention is a compound represented by the following general formula (I):

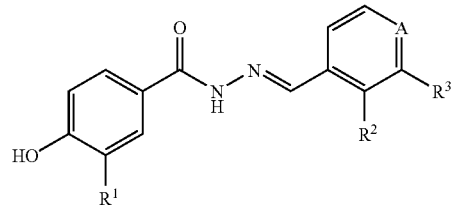

(I)

(wherein $R^1$ represents hydrogen, a halogen atom, a nitro group or a cyano group, $R^2$ represents hydrogen or a halogen atom or may, together with $R^3$, form an optionally substituted benzene ring or an optionally substituted pyrrole ring, $R^3$ represents hydrogen or a methoxy group or may, together with $R^2$, form an optionally substituted benzene ring or an optionally substituted pyrrole ring or may, together with $R^4$, form an optionally substituted benzene ring or an optionally substituted pyrrole ring, and A represents a nitrogen atom or C—$R^4$ whereupon $R^4$ represents hydrogen, an optionally substituted C1 to C6 alkyl group, —$OR^7$, —$NR^8R^9$, —NHCO—$R^{10}$ or —$SO_2$—$R^{11}$ or may, together with $R^3$, form an optionally substituted benzene ring or an optionally substituted pyrrole ring, $R^7$, $R^8$ and $R^9$ independently represent hydrogen or an optionally substituted C1 to C6 alkyl group, $R^{10}$ represents a C1 to C6 alkyl group, a C3 to C6 cycloalkyl group, an optionally substituted furyl group, an optionally substituted thienyl group, an optionally substituted benzyl group, an optionally substituted benzyloxymethyl group, an optionally substituted phenylvinyl group or an optionally substituted phenoxymethyl group, and $R^{11}$ represents an optionally substituted morpholyl group, an optionally substituted cyclopentylamino group, an optionally substituted piperidinyl group or a diethylamino group) or a pharmaceutically acceptable salt thereof.

Herein, $R^1$ is preferably not hydrogen, and the halogen atom represented by $R^1$ is preferably a bromine atom, a chlorine atom or a fluorine atom. The halogen atom represented by $R^2$ is also preferably a bromine atom, a chlorine atom or a fluorine atom. These also apply to the compounds in the following three groups.

In the present invention, the methylidene hydrazide compounds inhibiting the functions of GIP can be classified into the following important compound groups.

The first group is a group of compounds represented by the following formula:

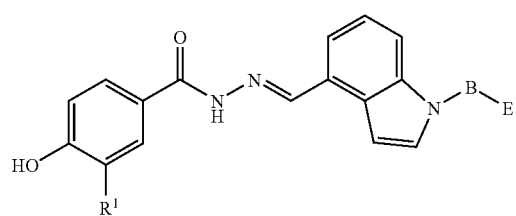

(I)

(wherein $R^1$ represents hydrogen, a halogen atom, a nitro group or a cyano group and B represents —CO—, —CO—

CH$_2$—, —CH$_2$CH$_2$O— or —CH(R$^{12}$)— whereupon R$^{12}$ represents hydrogen or a C1 to C6 alkyl group, and E represents an optionally substituted phenyl group, an optionally substituted 1,3-dioxaindanyl group, an optionally substituted naphthyl group, an optionally substituted pyridyl group, an optionally substituted pyrrolyl group, an optionally substituted thienyl group, an optionally substituted oxadiazolyl group, an optionally substituted thiazolyl group, an optionally substituted 2-phenyl[1,3]dioxolanyl group, an optionally substituted C3 to C6 cycloalkyl group, an optionally substituted quinoxalyl group or an optionally substituted benzothienyl group) or pharmaceutically acceptable salts thereof.

The second group is a group of compounds represented by the following formula:

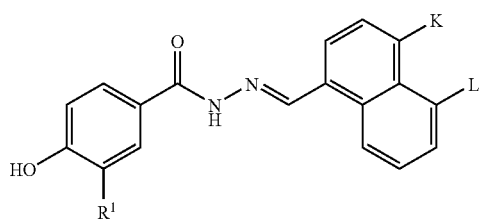

(wherein R$^1$ represents hydrogen, a halogen atom, a nitro group or a cyano group, K represents hydrogen, a C1 to C7 alkyl group substituted with a hydroxyl group, —NHCO—R$^{13}$—, —OR$^{14}$, —CH$_2$O—CONHR$^{15}$, —CH$_2$NH—R$^{16}$, —CH$_2$CO—NR$^{17}$R$^{18}$ or —SO$_2$—R$^{19}$, L represents hydrogen or —M—R$^{20}$ whereupon M represents —CH$_2$—, —CH$_2$OCH$_2$—, —CH$_2$—SO—CH$_2$—, or —CH$_2$—SO$_2$—CH$_2$—, R$^{13}$ represents a C1 to C6 alkyl group, a C3 to C6 cycloalkyl group, an optionally substituted furyl group, an optionally substituted thienyl group, an optionally substituted benzyl group, an optionally substituted benzyloxymethyl group, an optionally substituted phenylvinyl group or an optionally substituted phenoxymethyl group, R$^{14}$ represents hydrogen or an optionally substituted C1 to C6 alkyl group, R$^{15}$ represents an optionally substituted C1 to C6 alkyl group, a cyclohexyl group or an optionally substituted phenyl group, R$^{16}$ represents an optionally substituted carbamoylmethyl group, R$^{17}$ and R$^{18}$ independently represent hydrogen or an optionally substituted C1 to C6 alkyl group, or R$^{17}$ may, together with R$^{18}$, form a piperidinyl group, R$^{19}$ represents an optionally substituted morpholyl group, an optionally substituted cyclopentylamino group, an optionally substituted piperidinyl group or a diethylamino group, and R$^{20}$ represents an optionally substituted phenyl group, an optionally substituted benzylamino group, an optionally substituted benzylpiperazyl group, an optionally substituted piperidinyl group, an optionally substituted morpholyl group, an optionally substituted pyrrolidinyl group or a diethylaminocarbonylmethoxy group) or pharmaceutically acceptable salts thereof.

The third group is a group of compounds represented by the following formula:

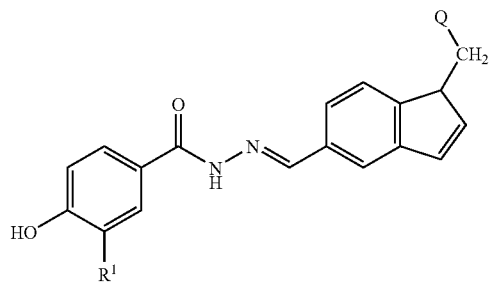

(wherein R$^1$ represents hydrogen, a halogen atom, a nitro group or a cyano group, and Q represents an optionally substituted phenyl group, an optionally substituted oxadiazolyl group, an optionally substituted thiazolyl group, an optionally substituted pyridyl group, an optionally substituted furyl group or an optionally substituted thienyl group) or pharmaceutically acceptable salts thereof.

Hereinafter, description will be given of the substituent groups and the like in more detail.

In this specification, the terms "optionally substituted" such as in the optionally substituted benzene ring are used plural times, and the terms "optionally substituted" mean that arbitrary ("arbitrary" also mean the case of plural, and the same after this) hydrogen(s) may be replaced by, for example, a C1 to C6 alkyl group, a trifluoromethyl group, a difluoromethyl group, a trifluoromethoxy group, a halogen atom, a carboxamide group, a hydroxymethyl group, a phenyl group, a dimethylamino group, a C1 to C6 alkyloxy group, or a nitro group.

Specific examples of the C1 to C6 alkyl group used throughout this specification may include a linear or branched alkyl group such as methyl, ethyl, propyl, isopropyl, butyl, isobutyl, tert-butyl, pentyl, and hexyl. Among these, the C1 to C3 alkyl group is preferable from the viewpoint of practical use. Similarly, specific examples of the C1 to C6 alkyloxy group may include linear or branched alkyloxy groups such as methyloxy, ethyloxy, propyloxy, isopropyloxy, butyloxy, isobutyloxy, tert-butyloxy, pentyloxy, and hexyloxy. Among these, the C1 to C3 alkyloxy group is preferable from the viewpoint of practical use. Specific examples of the C3 to C6 cycloalkyl group may include cyclic alkyl groups such as cyclopropyl, cyclobutyl, cyclopentyl, and cyclohexyl.

The pharmaceutically acceptable salts include, for example, the compounds which have formed acid addition salts with inorganic acids such as hydrochloric acid, hydrobromic acid and sulfuric acid, and organic acids such as oxalic acid, fumaric acid, maleic acid, tartaric acid and citric acid.

The methylidene hydrazide compound contained in the GIP function inhibitor according to the present invention is a well-known compound and can be produced by a method described in WO 00/39088 or a method described in *J. Med. Chem.*, Vol. 44, 3141–3149 (2001). Alternatively, it can be purchased from library suppliers such as ChemBridge Corporation.

The present invention relates to a GIP function inhibitor comprising the above-described methylidene hydrazide compound as the active ingredient and, also, to use of the compound for producing the GIP function inhibitor. It would be possible, but is not evident from test results, that the GIP function inhibitor is an antagonist of GIP receptor. The GIP function inhibitor according to the present invention is not only useful as a low-molecular compound elucidating the role of GIP in the living body, but also usable as an agent for preventing/ameliorating obesity. Usability of the GIP function inhibitor as an agent for preventing/ameliorating obesity is shown in K. Miyawaki et al., "Inhibition of GIP Signaling Prevents Obesity", abstract #335-PP, the 61st Scientific Sessions of American Diabetes Association (2001) and WO 01/87341 supra.

The administration form of the methylidene hydrazide compound according to the present invention can be selected, depending on the object, from various kinds of administration forms described in the general rules of pharmaceuticals in "the Japanese Pharmacopoeia". For example, orally ingestible ingredients usually used in this field may be used in forming tablets. Examples of such ingredients may include excipients such as lactose, crystalline cellulose, white sugar, and potassium phosphate. If necessary, various additives used conventionally in pharmaceutical manufacturing, such as binders, disintegrators, lubricants and suspending agents, may be incorporated.

The amount of the active ingredient represented by the general formula (I) to be contained in the pharmaceutical preparation of the present invention is not particularly limited, and is suitably selected from a broad range. The amount of the active ingredient is suitably selected depending on usage, the age, sex and other conditions of the patient and the severity of disease, but usually the compound according to the present invention is given in an amount of about 0.01 to 500 mg per kg of body weight a day. The pharmaceutical preparation can be administered in one to four divided portions a day. However, the dose and administration frequency shall be determined in view of related situations including the degree of conditions to be treated, selection of the compound to be administered, and selected administration route; thus, the scope of the present invention is not limited by the range of the dose and the administration frequency described above.

EXAMPLES

Hereinafter, description will be given of the present invention in more detail by way of examples and reference examples; however, the present invention is not limited thereto.

Methylidene hydrazide compounds to be subjected to pharmacological tests are compounds described in *J. Med. Chem.*, Vol. 44, 3141–3149 (2001) or compounds described in WO 00/39088. As typical compounds, the following compounds were subjected to the pharmacological tests.

Compound 1: 4-Hydroxybenzoic acid 2-bromobenzylidene)hydrazide

Compound 1 shown below was purchased from ChemBridge Corporation.

(Chemical Formula Representing Compound 1)

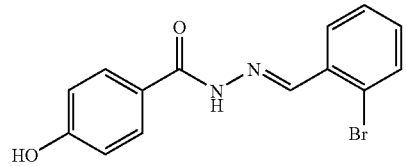

Compound 2: 3-Cyano-4-hydroxybenzoic acid [1-(2,3,5,6-tetramethylbenzyl)indol-4-yl]methylidene hydrazide Compound 2 shown below was synthesized by the method described in WO 00/39088.

(Chemical Formula Representing Compound 2)

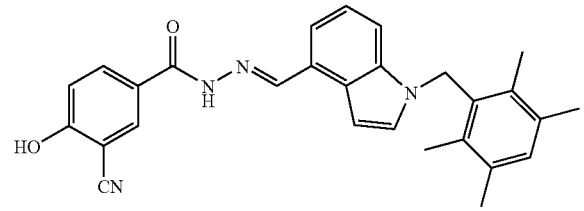

Compound 3: 3-Chloro-4-hydroxybenzoic acid (4-methoxynaphthalen-1-yl)methylidene hydrazide Compound 3 shown below was synthesized by the method described in *J. Med. Chem.*, Vol. 44, 3141–3149 (2001).

(Chemical Formula Representing Compound 3)

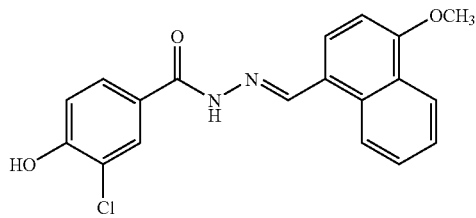

Compound 4: 3-Chloro-4-hydroxybenzoic acid [1-(5-chlorothiophen-2-ylmethyl)-1H-indol-5-yl]methylidene hydrazide Compound 4 shown below was synthesized by the method described in WO 00/39088.

(Chemical Formula Representing Compound 4)

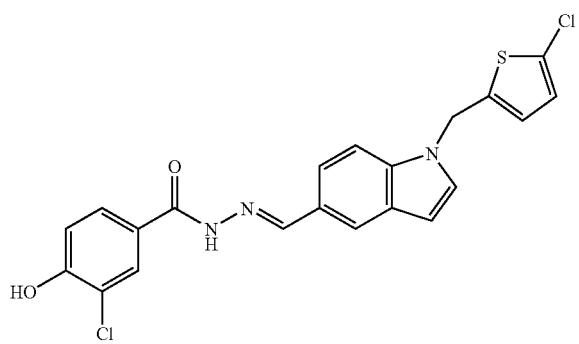

Next, description will be given of test examples using Compounds 1 to 4.

Pharmacological Test Example 1

The system for evaluation of GIP function inhibitors (GIP receptor antagonists and the like) made use of the following method wherein their inhibitory activity on production of cAMP as GIP intracellular transmitter was used as an indicator.

According to a method of Kubota et al. (Diabetes 45: 1701–1705, 1996), human GIP receptor-expressing cells prepared by introducing GIP cDNA into CHO cells were used. First, cAMP was produced by stimulation with 100 pM GIP in the presence/absence of the test chemical at 37° C. for 30 minutes in phosphate-buffered saline, pH 7.4, containing 1 mM isobutylmethylxanthine, 5.6 mM glucose and 0.5% bovine serum albumin. Then, using a cAMP assay system (PE Biosystems), the cells were lyzed with an attached lysis buffer, the amount of cAMP accumulated in the cells was measured, and the inhibitory activity of the test sample on the functions of GIP was determined. To verify the action of the test sample completely irrelevant to the action on GIP receptor, the inhibitory effect of the test sample on formation of cAMP upon stimulating, with 5 μM forskolin, CHO cells into which the GIP receptor gene had not been introduced (cells not expressing the GIP receptor) was also confirmed. The inhibitory activity was expressed in terms of $IC_{50}$ (concentration of the compound at which the production of cAMP by GIP is inhibited by 50%). A compound not showing any inhibitory activity on formation of cAMP in the cells not expressing the GIP receptor, but inhibiting the formation of cAMP by stimulation with GIP, in the cells expressing the GIP receptor, was regarded as an active compound. A dose/inhibition curve in this measurement is shown in FIG. 1, and the calculation results of $IC_{50}$ are shown in Table 1.

TABLE 1

| Test Compound | $IC_{50}$ (μM) |
| --- | --- |
| Compound 1 | 19 |
| Compound 2 | 0.0063 |
| Compound 3 | 0.56 |
| Compound 4 | 0.44 |

Compounds 1 to 4 did not exhibit any inhibitory activity on cAMP formation upon stimulation with forskolin in the cells not expressing GIP receptor, but inhibited cAMP formation upon stimulation with GIP in the cells expressing the GIP receptor. That is, Compounds 1 to 4 were revealed to inhibit the functions of GIP.

From detailed analysis, it can be estimated that because Compound 1 inhibited the functions of GIP though at low levels, the essential structure showing the inhibitory activity is 4-hydroxybenzoic acid benzylidene hydrazide. It can also be estimated that the activity is improved by introducing a chloride atom, a fluorine atom, a nitro group or a cyano group at the ortho-position with respect to the hydroxyl group or by changing the benzylidene group into an indole-4-methylidene group or a naphthalene-1-methylidene group. It follows that for example, Compound 2 can be estimated to be an active compound because it is an indol-4-ylmethylidene hydrazide derivative, that is, a compound having the essential structure wherein a cyano group is introduced at the ortho-position with respect to the hydroxyl group and the benzylidene group is changed into an indole-4-methylidene group.

Pharmacological Test Example 2

For confirming the receptor selectivity of the test sample, the inhibitory activity of the test sample on formation of cAMP upon stimulation with GLP-1 (60 pM) in CHO cells expressing a receptor of GLP-1, which, like GIP, belongs to the glucagon/secretin family, was confirmed at the concentration of $IC_{50}$ on the GIP receptor. As a comparative control, 500 nM GIP(7–30) —$NH_2$ (tGIP) was used. Similar to tGIP, Compounds 1 to 4 did not exhibit any inhibitory activity on formation of cAMP upon stimulation with GLP-1, in the cells expressing the GLP-1 receptor.

The invention claimed is:

1. A method to treat obesity resulting from GIP function in a mammal comprising administering to the subject an effective amount of a compound represented by the following general formula (I):

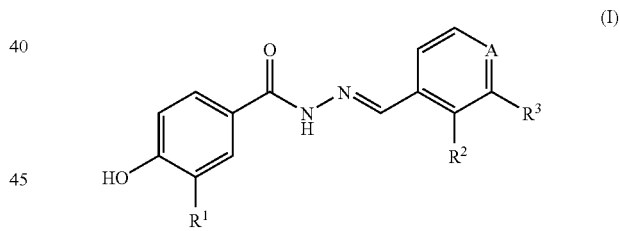

(wherein $R^1$ represents hydrogen, a halogen atom, a nitro group or a cyano group, $R^2$ represents hydrogen or a halogen atom or may, together with $R^3$, form an optionally substituted benzene ring or an optionally substituted pyrrole ring, $R^3$ represents hydrogen or a methoxy group or may, together with $R^2$, form an optionally substituted benzene ring or an optionally substituted pyrrole ring or may, together with $R^4$, form an optionally substituted benzene ring or an optionally substituted pyrrole ring, and A represents a nitrogen atom or C—$R^4$ whereupon $R^4$ represents hydrogen, an optionally substituted C1 to C6 alkyl group, —$OR^7$, —$NR^8R^9$, —NHCO—$R^{10}$ or —$SO_2$—$R^{11}$ or may, together with $R^3$, form an optionally substituted benzene ring or an optionally substituted pyrrole ring, $R^7$, $R^8$ and $R^9$ independently represent hydrogen or an optionally substituted C1 to C6 alkyl group, $R^{10}$ represents a C1 to C6 alkyl group, a C3 to C6 cycloalkyl group, an optionally substituted furyl group, an optionally substituted thienyl group, an optionally substituted benzyl group, an optionally substituted benzyloxymethyl group, an optionally substituted phenylvinyl group or an optionally substituted phenoxymethyl group, and $R^{11}$ represents an optionally substituted morpholyl group, an optionally substituted cyclopentylamino group, an optionally substituted piperidinyl group or a diethylamino group) or a pharmaceutically acceptable salt thereof.

2. The method to treat obesity resulting from GIP function according to claim 1, wherein the compound is represented by the following general formula:

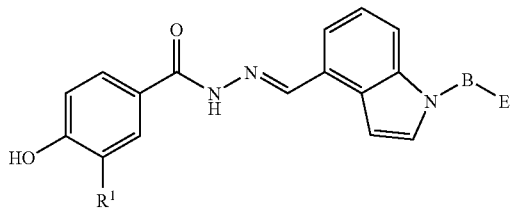

(wherein $R^1$ represents hydrogen, a halogen atom, a nitro group or a cyano group and B represents —CO—, —CO—CH$_2$—, —CH$_2$CH$_2$O— or —CH(R$^{12}$)— whereupon $R^{12}$ represents hydrogen or a C1 to C6 alkyl group, and E represents an optionally substituted phenyl group, an optionally substituted 1,3-dioxaindanyl group, an optionally substituted naphthyl group, an optionally substituted pyridyl group, an optionally substituted pyrrolyl group, an optionally substituted thienyl group, an optionally substituted oxadiazolyl group, an optionally substituted thiazolyl group, an optionally substituted 2-phenyl[1,3]dioxolanyl group, an optionally substituted C3 to C6 cycloalkyl group, an optionally substituted quinoxalyl group or an optionally substituted benzothienyl group) or a pharmaceutically acceptable salt thereof.

3. The method to treat obesity resulting from GIP function according to claim 1, wherein the compound is represented by the following general formula:

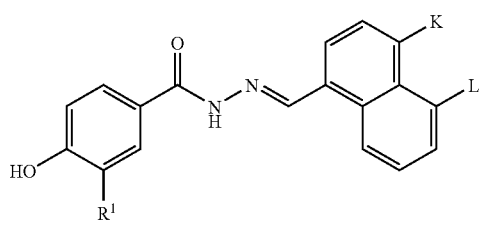

(wherein $R^1$ represents hydrogen, a halogen atom, a nitro group or a cyano group, K represents hydrogen, a C1 to C6 alkyl group substituted with a hydroxyl group, —NHCO—$R^{13}$—, —OR$^{14}$, —CH$_2$O—CONHR$^{15}$, —CH$_2$NH—R$^{16}$, —CH$_2$CO—NR$^{17}$R$^{18}$ or —SO$_2$—R$^{19}$, L represents hydrogen or —M—R$^{20}$ whereupon M represents —CH$_2$—, —CH$_2$OCH$_2$—, —CH$_2$—SO—CH$_2$—, or —CH$_2$—SO$_2$—CH$_2$—, $R^{13}$ represents a C1 to C6 alkyl group, a C3 to C6 cycloalkyl group, an optionally substituted furyl group, an optionally substituted thienyl group, an optionally substituted benzyl group, an optionally substituted benzyloxymethyl group, an optionally substituted phenylvinyl group or an optionally substituted phenoxymethyl group, $R^{14}$ represents hydrogen or an optionally substituted C1 to C6 alkyl group, $R^{15}$ represents an optionally substituted C1 to C6 alkyl group, a cyclohexyl group or an optionally substituted phenyl group, $R^{16}$ represents an optionally substituted carbamoylmethyl group, $R^{17}$ and $R^{18}$ independently represent hydrogen or an optionally substituted C1 to C6 alkyl group, or $R^{17}$ may, together with $R^{18}$, form a piperidinyl group, $R^{19}$ represents an optionally substituted morpholyl group, an optionally substituted cyclopentylamino group, an optionally substituted piperidinyl group or a diethylamino group, and $R^{20}$ represents an optionally substituted phenyl group, an optionally substituted benzylamino group, an optionally substituted benzylpiperazyl group, an optionally substituted piperidinyl group, an optionally substituted morpholyl group, an optionally substituted pyrrolidinyl group or a diethylaminocarbonylmethoxy group) or a pharmaceutically acceptable salt thereof.

4. The method to treat obesity resulting from GIP function according to claim 1, wherein the compound is represented by the following general formula:

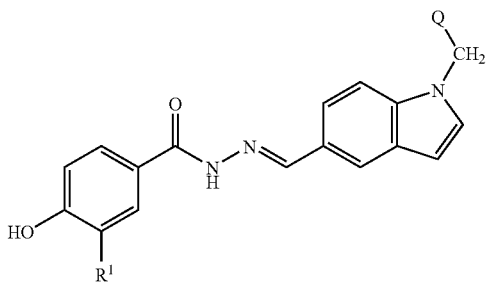

(wherein $R^1$ represents hydrogen, a halogen atom, a nitro group or a cyano group, and Q represents an optionally substituted phenyl group, an optionally substituted oxadiazolyl group, an optionally substituted thiazolyl group, an optionally substituted pyridyl group, an optionally substituted furyl group or an optionally substituted thienyl group) or a pharmaceutically acceptable salt thereof.

5. A method for preventing/ameliorating obesity in a mammal comprising administering to the subject an effective amount of a compound represented by the following general formula (I):

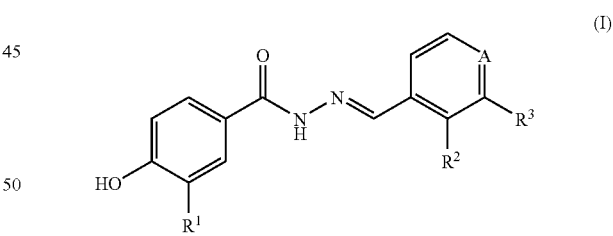

(I)

(wherein $R^1$ represents hydrogen, a halogen atom, a nitro group or a cyano group, $R^2$ represents hydrogen or a halogen atom or may, together with $R^3$, form an optionally substituted benzene ring or an optionally substituted pyrrole ring, $R^3$ represent hydrogen or a methoxy group or may, together with $R^2$, form an optionally substituted benzene ring or an optionally substituted pyrrole ring or may, together with $R^4$, form an optionally substituted benzene ring or an optionally substituted pyrrole ring, and A represents a nitrogen atom or C—$R^4$ whereupon $R^4$ represents hydrogen, an optionally substituted C1 to C6 alkyl group, —OR$^7$, —NR$^8$R$^9$, —NHCO—R$^{10}$ or —SO$_2$—R$^{11}$ or may, together with $R^3$, form an optionally substituted benzene ring or an optionally substituted pyrrole ring, $R^7$, $R^8$ and $R^9$ independently represent hydrogen or an optionally substituted C1 to C6 alkyl group, $R^{10}$ represents a C1 to C6 alkyl group, a C3 to C6 cycloalkyl group, an optionally substituted furyl group, an optionally substituted thienyl group, an optionally substituted benzyl group, an optionally substituted benzyloxymethyl group, an optionally substituted phenylvinyl group or an optionally substituted phenoxymethyl group, and $R^{11}$ represents an optionally substituted morpholyl group, an optionally substituted cyclopentylamino group, an optionally substituted piperidinyl group or a diethylamino group) or a pharmaceutically acceptable salt thereof.

6. The method for preventing/ameliorating obesity according to claim 5, wherein the compound is represented by the following general formula:

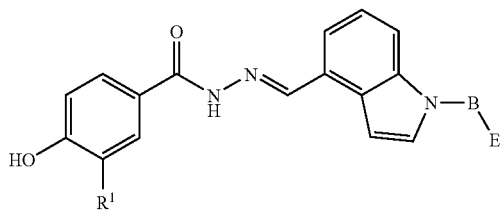

(wherein $R^1$ represents hydrogen, a halogen atom, a nitro group or a cyano group and B represents —CO—, —CO—CH$_2$—, —CH$_2$CH$_2$O— or —CH($R^{12}$)— whereupon $R^{12}$ represents hydrogen or a C1 to C6 alkyl group, and E represents an optionally substituted phenyl group, an optionally substituted 1,3-dioxaindanyl group, an optionally substituted naphthyl group, an optionally substituted pyridyl group, an optionally substituted pyrrolyl group, an optionally substituted thienyl group, an optionally substituted oxadiazolyl group, an optionally substituted thiazolyl group, an optionally substituted 2-phenyl[1,3]dioxolanyl group, an optionally substituted C3 to C6 cycloalkyl group, an optionally substituted quinoxalyl group or an optionally substituted benzothienyl group) or a pharmaceutically acceptable salt thereof.

7. The method for preventing/ameliorating obesity according to claim 5, wherein the compound is represented by the following general formula:

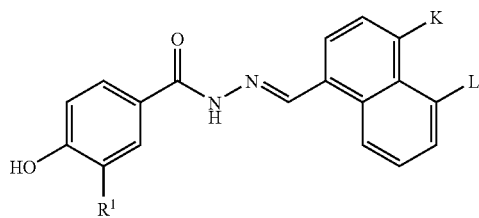

(wherein $R^1$ represents hydrogen, a halogen atom, a nitro group or a cyano group, K represents hydrogen, a C1 to C6 alkyl group substituted with a hydroxyl group, —NHCO—$R^{13}$—, —OR$^{14}$, —CH$_2$O—CONHR$^{15}$, —CH$_2$NH—R$^{16}$, —CH$^2$CO—NR$^{17}$R$^{18}$ or —SO$_2$—R$^{19}$, L represents hydrogen or —M—R$^{20}$ whereupon M represents —CH$_2$—, —CH$_2$OCH$_2$—, —CH$_2$—SO—CH$_2$—, or —CH$_2$—SO$_2$—CH$_2$—, $R^{13}$ represents a C1 to C6 alkyl group, a C3 to C6 cycloalkyl group, an optionally substituted furyl group, an optionally substituted thienyl group, an optionally substituted benzyl group, an optionally substituted benzyloxymethyl group, an optionally substituted phenylvinyl group or an optionally substituted phenoxymethyl group, $R^{14}$ represents hydrogen or an optionally substituted C1 to C6 alkyl group, $R^{15}$ represents an optionally substituted C1 to C6 alkyl group, a cyclohexyl group or an optionally substituted phenyl group, $R^{16}$ represents an optionally substituted carbamoylmethyl group, $R^{17}$ and $R^{18}$ independently represent hydrogen or an optionally substituted C1 to C6 alkyl group, or $R^{17}$ may, together wit $R^{18}$, form a piperidinyl group, $R^{19}$ represents an optionally substituted morpholyl group, an optionally substituted cyclopentylamino group, an optionally substituted piperidinyl group or a diethylamino group, and $R^{20}$ represents an optionally substituted phenyl group, an optionally substituted benzylamino group, an optionally substituted benzylpiperazyl group, an optionally substituted piperidinyl group, an optionally substituted morpholyl group, an optionally substituted pyrrolidinyl group or a diethylaminocarbonylmethoxy group) or a pharmaceutically acceptable salt thereof.

8. The method for preventing/ameliorating obesity according to claim 5 wherein the compound is represented by the following general formula:

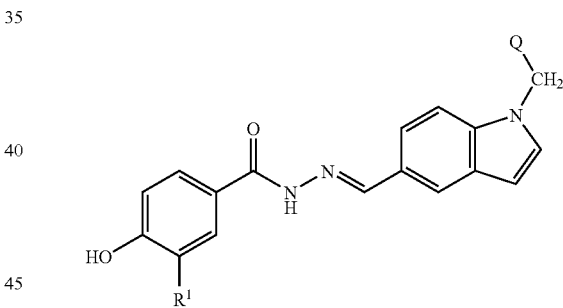

(wherein $R^1$ represents hydrogen, a halogen atom, a nitro group or a cyano group, and Q represents an optionally substituted phenyl group, an optionally substituted oxadiazolyl group, an optionally substituted thiazolyl group, an optionally substituted pyridyl group, an optionally substituted furyl group or an optionally substituted thienyl group) or a pharmaceutically acceptable salt thereof.

* * * * *